(12) United States Patent
Vittorio

(10) Patent No.: US 8,524,690 B2
(45) Date of Patent: Sep. 3, 2013

(54) DNA POLYMERASE INHIBITORS COMPOSITION AND METHODS

(75) Inventor: Carmela Vittorio, Ardmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/597,745

(22) PCT Filed: Apr. 28, 2008

(86) PCT No.: PCT/US2008/005425
§ 371 (c)(1),
(2), (4) Date: Feb. 3, 2010

(87) PCT Pub. No.: WO2008/134033
PCT Pub. Date: Nov. 6, 2008

(65) Prior Publication Data
US 2010/0137341 A1    Jun. 3, 2010

Related U.S. Application Data

(60) Provisional application No. 60/907,997, filed on Apr. 26, 2007.

(51) Int. Cl.
*A61K 31/66* (2006.01)

(52) U.S. Cl.
USPC .................. 514/75; 514/79; 514/85; 514/120

(58) Field of Classification Search
None
See application file for complete search history.

(56) References Cited

U.S. PATENT DOCUMENTS

| | | | |
|---|---|---|---|
| 5,645,825 A | 7/1997 | Hillebrand | |
| 5,770,582 A | 6/1998 | Von Borstel | |
| 6,136,835 A * | 10/2000 | Camden | 514/383 |
| 6,337,324 B1 * | 1/2002 | Harmenberg et al. | 514/171 |
| 6,469,015 B1 | 10/2002 | Griffiths | |
| 6,884,772 B1 | 4/2005 | Ohuchi | |
| 2005/0287098 A1 | 12/2005 | Sun et al. | |
| 2006/0057088 A1 | 3/2006 | Tankovich | |
| 2006/0135464 A1 | 6/2006 | Johnson | |

FOREIGN PATENT DOCUMENTS

GB    2310139    8/1997

OTHER PUBLICATIONS

Areias et al., One Year of Lamivudine Therapy for Portuguese Patients with Chronic Hepatitis B, Clin. Drug Invest 2003, 23(5): 339-346.*
Abamba, G., Skin Preparations, section 14.2—Biology of the Skin, pp. 393-405, in Poucher's Perfumes, Cosmetics and Soaps, 10th ed., ed. Hilda Butler, Kluwer Academic Publishers, 2000.*
Hertel et al., Evaluation of Antitumor Activity of Gemcitabine (2',2'-Difluoro-2'-deoxycytidine), Cancer Research 50, 4417-4422, Jul. 15, 1990.*
Kroep et al., Phase II study of cisplatin preceding gemcitabine in patients with advanced oesophageal cancer, Annals of Oncology, 15: 230-235, 2004.*
Sorensen et al., Phase II study of gemcitabine and vindesine in patients with previously untreated non-resectable non-small-cell lung cancer, British Journal of Cancer (1999), 79 (5/6), 875-881.*
D'Antiga et al., Combined Lamivudine/ Interferon-_Treatment in 'Immunotolerant' Children Perinatally Infected with Hepatitis B: A Pilot Study, J. Pediatr., 2006, 148: 228-33.*
Calista et al., "Topical cidofovir for severe cutaneous human papillomavirus and molluscum contagiosum infections in patients with HIV/AIDS. A pilot study", J. of the European Academy of Dermatology and Venerology, vol. 14, No. 6, pp. 484-488, Nov. 2000.
Martin et al., "Nursing considerations in the use of cidofovir for CMV Retinitis in patients with AIDS: Report of a roundtable meeting", Journal of the Association of Nurses in Aids Care, vol. 8, No. 5, p. 72, 1997.
Fong, "Hair loss associated with lamivudine", Lancet, vol. 344, No. 8938, p. 1702, 1994.
Imen et al., "Bullous dermatosis associated with gemcitabine therapy for non-small-cell lung carcinoma", Respiratory Medicine, vol. 100, No. 8, pp. 1463-1465, 2006.
Galmarini et al., "Nucleoside analogues and nucleobases in cancer treatment", Lancet Oncology, vol. 3, No. 7, pp. 415-424, 2002.
Langer, "New methods of drug delivery", Science 249:1527-1533 (1990).
Treat et al., "Liposome encapsulated doxorubicin preliminary results of phase I and phase II trials", Liposomes in the Therapy of Infectious Disease and Cancer, pp. 363-366 (1989).
Lopez-Berestein, "Treatment of systemic fungal infections with liposomal amphotecerin B", Liposomes in the Therapy of Infectious Disease and Cancer, pp. 317-327 (1989).

* cited by examiner

*Primary Examiner* — Sreeni Padmanabhan
*Assistant Examiner* — Svetlana M Ivanova
(74) *Attorney, Agent, or Firm* — Mark S. Cohen; Pearl Cohen Zedek Latzer Baratz LLP

(57) ABSTRACT

A topical composition containing a DNA polymerase inhibitor for removing hair as well as methods of inducing hair loss is described.

8 Claims, No Drawings

DNA POLYMERASE INHIBITORS COMPOSITION AND METHODS

CROSS-REFERENCE TO RELATED APPLICATIONS

This application is a National Phase Application of PCT International Application PCT/US08/05425, filed Apr. 28, 2008, that claims priority to U.S. Provisional Application 60/907,997, filed Apr. 26, 2007, which is incorporated by reference herein in it's entirety.

BACKGROUND OF THE INVENTION

DNA polymerase inhibitors are commercially available to inhibit the replication of DNA viruses (cidofovir [Visitide®], valacyclovir hydrochloride [Valtrex®], famciclovir [Famvir®, acyclovir [Zovirax]). They also have an affinity for mammalian DNA, but to a lesser extent. Each of these currently available drugs has various degrees of affinity for DNA polymerase inhibition. Acyclovir is an effective drug for the treatment of Herpes Simplex Virus (HSV) and Varicella-Zoster Virus (VZV) infections, which after phosphorylation to the triphosphate inhibits viral DNA polymerase. Acyclovir has low oral bioavailability, therefore prodrugs have been developed, such as the L-valyl ester, valaciclovir, that treats shingles. Ganciclovir is used against Cyto-Megalo-Virus CMV, and famciclovir, a lipophilic prodrug of penciclovir, is marketed for shingles. The acyclic nucleoside phosphonates are active against thymidine kinase-resistant viral strains. Oligonucleotides incorporating acyclic nucleosides at the 3'- and 5'-ends, or constituted of amino acyclic nucleosides, are resistant to cleavage by nucleases and may be useful in antisense and/or antigene therapy. Some acyclic nucleosides are potent inhibitors of purine and pyrimidine nucleoside phosphorylase.

Nucleoside phosphonates (ANPs) bring a new dimension to the therapy of viral infections, as they offer a broader spectrum of activity, a longer duration of antiviral action and a lower risk of resistance development compared with available treatments. The key factor underlying all these unique features is the presence of the phosphonate group, which allows ANPs to interfere with the normal pathway of nucleic acid biosynthesis, and, in particular, viral nucleic acid biosynthesis. Three ANPs (cidofovir, adefovir and tenofovir) have been marketed worldwide. They are active against virtually all key DNA viruses and retroviruses.

ANPs behave as analogues of 2',3'-dideoxynucleotides. In contrast to the 'classical' acyclic nucleoside analogues, such as acyclovir, ganciclovir or penciclovir, or dideoxynucleoside analogues, such as zidovudine (AZT) or lamivudine (3TC), they do not require the initial phosphorylation needed for the activation of modified nucleosides, which is catalysed by nucleoside kinase. In those cells in which the nucleoside kinase is less active or completely missing, nucleoside analogues are inactive, whereas ANPs are converted by nucleotide kinase (GMP kinase or AMP kinase) to the monophosphate (an analogue of diphosphate) and further by nucleoside diphosphate (NDP) kinase to the triphosphate analogue. These di- and triphosphate analogues are inhibitors/substrates of the respective enzymes. However, the true active species are the triphosphate (ANPpp) analogues that target DNA polymerase—viral and/or cellular. The inhibition differs with the character of the base, with the most potent inhibition occurring with guanine derivatives. This was observed with DNA polymerase from different sources—viral and mammalian, as well as with enzymes from transformed cells or cellular parasites. However, ANPpp analogues are also substrates of DNA polymerases: consequently, the elongation of the DNA chain catalysed by diverse DNA polymerases and Reverse transcriptases (RTs) comes to a standstill after the incorporation of 9-[2-(phosphonomethoxy) ethyl] (PME) or (R)- or (S)-9-[2-(phosphonomethoxy)propyl] (PMP) compounds—a situation that is typical of chain-terminators (for example, AZT and 3TC).

The antiviral activity of ANPs is the result of the higher affinity of the diphosphorylated ANP metabolite for viral DNA polymerases (that is, HSV-1 DNA polymerase, CMV DNA polymerase and HIV-1 RT) than for the cellular DNA polymerases. As conversion of the ANPs to the monophosphate stage does not depend on the virus-induced thymidine kinase (as opposed to, for example, the antiherpes drug acyclovir), they should exert activity against a broad range of DNA viruses. Indeed, all DNA viruses and retroviruses have been found to be susceptible to cidofovir, adefovir and/or tenofovir. Cidofovir ((S)-1-[3-hydroxy-2-(phosphonylmethoxy)propyl]cytosine (HPMPC)) is phosphorylated by pyrimidine nucleoside monophosphate kinase to cidofovir monophosphate (HPMPCp), which is then further phosphorylated by nucleoside diphosphate kinase, pyruvate kinase or creatine kinase to cidofovir diphosphate (HPMPCpp). These two phosphorylation steps can occur in both uninfected and virus-infected cells. For adefovir (PMEA), and presumably also for tenofovir ((R)-9-[2-(phosphono-methoxy)propyl]adenine; PMPA), phosphorylation to the diphosphate form (PMEApp and PMPApp, respectively) requires two steps, both of which depend on the AMP (dAMP) kinase.

Cidofovir (a nucleoside analogue of deoxycytidine) is an intravenous anti-viral drug most active against DNA viruses (such as Human Papilloma, pox, and herpes simplex). Cidofovir has proved to be effective in the treatment of herpes-, papilloma-, polyoma-, adeno- and pox-virus infections. It has been formally approved for intravenous use in the treatment of cytomegalovirus retinitis in AIDS patients.

SUMMARY OF THE INVENTION

This invention relates, in another embodiment, to a topical dermal pharmaceutical composition comprising more than 0.0001% and less than 1% DNA polymerase inhibitor.

In another embodiment, the present invention provides a method of inducing hair loss in a subject, comprising topically administering to a subject a composition comprising a DNA polymerase inhibitor, thereby inducing hair loss.

In another embodiment, the present invention provides a method of inhibiting hair growth in a subject, comprising topically administering to a subject a composition comprising a DNA polymerase inhibitor, thereby inhibiting hair growth.

DETAILED DESCRIPTION OF THE PRESENT INVENTION

In one embodiment, the present invention provides a pharmaceutical composition comprising more than 0.0001% and less than 1% DNA polymerase inhibitor. In another embodiment, the pharmaceutical composition of the present invention is a topical pharmaceutical composition. In another embodiment, the pharmaceutical composition of the present invention is a topical dermal pharmaceutical composition. In another embodiment, the DNA polymerase inhibitor concentration of the present invention is expressed as a weight/weight percentage.

In another embodiment, the pharmaceutical composition of the present invention contains from about 0.0001% to 0.0005% DNA polymerase inhibitor. In another embodiment, the pharmaceutical composition of the present invention contains from about 0.0005% to 0.001% DNA polymerase inhibitor. In another embodiment, the pharmaceutical composition of the present invention contains from about 0.001% to 0.005% DNA polymerase inhibitor. In another embodiment, the pharmaceutical composition of the present invention contains from about 0.005% to 0.0075% DNA polymerase inhibitor. In another embodiment, the pharmaceutical composition of the present invention contains from about 0.0075% to 0.01% DNA polymerase inhibitor. In another embodiment, the pharmaceutical composition of the present invention contains from about 0.01% to 0.015% DNA polymerase inhibitor. In another embodiment, the pharmaceutical composition of the present invention contains from about 0.015% to 0.025% DNA polymerase inhibitor. In another embodiment, the pharmaceutical composition of the present invention contains from about 0.025% to 0.035% DNA polymerase inhibitor. In another embodiment, the pharmaceutical composition of the present invention contains from about 0.035% to 0.045% DNA polymerase inhibitor. In another embodiment, the pharmaceutical composition of the present invention contains from about 0.045% to 0.055% DNA polymerase inhibitor. In another embodiment, the pharmaceutical composition of the present invention contains from about 0.055% to 0.065% DNA polymerase inhibitor. In another embodiment, the pharmaceutical composition of the present invention contains from about 0.065% to 0.075% DNA polymerase inhibitor. In another embodiment, the pharmaceutical composition of the present invention contains from about 0.075% to 0.1% DNA polymerase inhibitor. In another embodiment, the pharmaceutical composition of the present invention contains from about 0.1% to 0.2% DNA polymerase inhibitor. In another embodiment, the pharmaceutical composition of the present invention contains from about 0.2% to 0.3% DNA polymerase inhibitor. In another embodiment, the pharmaceutical composition of the present invention contains from about 0.3% to 0.4% DNA polymerase inhibitor. In another embodiment, the pharmaceutical composition of the present invention contains from about 0.4% to 0.5% DNA polymerase inhibitor. In another embodiment, the pharmaceutical composition of the present invention contains from about 0.5% to 0.6% DNA polymerase inhibitor. In another embodiment, the pharmaceutical composition of the present invention contains from about 0.6% to 0.7% DNA polymerase inhibitor. In another embodiment, the pharmaceutical composition of the present invention contains from about 0.7% to 0.8% DNA polymerase inhibitor. In another embodiment, the pharmaceutical composition of the present invention contains from about 0.8% to 0.9% DNA polymerase inhibitor. In another embodiment, the pharmaceutical composition of the present invention contains from about 0.9% to 0.99% DNA polymerase inhibitor. In another embodiment, the pharmaceutical composition of the present invention contains from about 1% to 2% DNA polymerase inhibitor. In another embodiment, the pharmaceutical composition of the present invention contains from about 1% to 3% DNA polymerase inhibitor. In another embodiment, the pharmaceutical composition of the present invention contains from about 3% to 6% DNA polymerase inhibitor. In another embodiment, the pharmaceutical composition of the present invention contains from about 2% to 5% DNA polymerase inhibitor. In another embodiment, the pharmaceutical composition of the present invention contains from about 4% to 8% DNA polymerase inhibitor. In another embodiment, the pharmaceutical composition of the present invention contains from about 5% to 10% DNA polymerase inhibitor. In another embodiment, the pharmaceutical composition of the present invention contains from about 10% to 15% DNA polymerase inhibitor. In another embodiment, the pharmaceutical composition of the present invention contains from about 15% to 20% DNA polymerase inhibitor. In another embodiment, the pharmaceutical composition of the present invention contains from about 20% to 30% DNA polymerase inhibitor. In another embodiment, the pharmaceutical composition of the present invention contains from about 30% to 40% DNA polymerase inhibitor. In another embodiment, the pharmaceutical composition of the present invention contains from about 40% to 50% DNA polymerase inhibitor. In another embodiment, the pharmaceutical composition of the present invention contains from about 50% to 60% DNA polymerase inhibitor. In another embodiment, the pharmaceutical composition of the present invention contains from about 60% to 80% DNA polymerase inhibitor. In another embodiment, the pharmaceutical composition of the present invention contains from about 80% to 100% DNA polymerase inhibitor.

The term "topical" as used in the present invention refers, in another embodiment, to a topical medication applied to body surfaces such as the skin or mucous membranes such as the vagina, penis, anus, throat, eye or the ear.

In another embodiment, the composition of the present invention is in an ointment dosage form. In another embodiment, an ointment is a viscous semisolid preparation used topically on a variety of body surfaces. In some embodiments, these body surfaces include the skin and the mucus membranes of the eye, vagina, anus, glans and nose. In another embodiment, the DNA polymerase inhibitor of the present invention is dissolved in the ointment. In another embodiment, the DNA polymerase inhibitor of the present invention is dispersed in an ointment.

In another embodiment, the composition of the present invention is in a lotion dosage form. In another embodiment, a lotion is a low- to medium-viscosity topical preparation intended for application to unbroken skin. In another embodiment, a lotion is a low viscosity topical preparation intended for application to unbroken skin. In another embodiment, a lotion is a medium-viscosity topical preparation intended for application to unbroken skin. In another embodiment, a lotion is an oil-in-water emulsion.

In some embodiments, lotion emulsion is the aqueous and oily phases, an emulgent to prevent separation of these two phases, and the DNA polymerase inhibitor. In some embodiments, other ingredients such as fragrances, glycerol, petroleum jelly, dyes, preservatives, proteins and stabilizing agents are added to the lotion of the present invention. In another embodiment, the DNA polymerase inhibitor of the present invention is dissolved in the lotion. In another embodiment, the DNA polymerase inhibitor of the present invention is dispersed in a lotion.

In another embodiment, the composition of the present invention is in a cream dosage form. In another embodiment, the cream of the present invention is a topical preparation. In another embodiment, the cream of the present invention is a topical preparation for application to the skin. In another embodiment, a cream of the present invention is applied to mucus membranes such as those of the rectum. In another embodiment, a cream of the present invention is applied to mucus membranes such as those of the vagina.

In another embodiment, the cream of the present invention is a semi-solid emulsion that is mixtures of oil and water. In another embodiment, the cream of the present invention is an oil-in-water (O/W) cream. In another embodiment, O/W cream is composed of small droplets of oil dispersed in a continuous aqueous phase. In another embodiment, the cream of the present invention is water-in-oil (W/O) cream. In another embodiment W/O cream is composed of small droplets of water dispersed in a continuous oily phase. In another embodiment, the DNA polymerase inhibitor of the present invention is dissolved in the cream. In another embodiment, the DNA polymerase inhibitor of the present invention is dispersed in a cream.

In another embodiment, Cidofovir is compounded in Dermavan® base (a water and glycerol stearate cream). In another embodiment, Cidofovir is compounded in Vanicream® base (commercially available emollient cream).

In another embodiment, the present invention comprises a dermal patch comprising the composition of the present invention. In another embodiment, the dermal patch of the present invention comprises an internal reservoir or a polymer matrix as a carrier for the DNA polymerase inhibitor which is supported by protective skins, e.g., polyethylene, for structural integrity. In another embodiment, the dermal patch of the present invention comprises polymeric gels based on hydrated polymers. In some embodiments, polymeric gels are cross linked to provide structural integrity. In another embodiment, the dermal patch of the present invention has high degree of flexibility and structural integrity, In another embodiment, the dermal patch is physiologically compatible, have good oxygen permeability and a high water content, and can carry and deliver a DNA polymerase inhibitor. In another embodiment, the dermal patch of the present invention delivers a DNA polymerase inhibitor to the dermal surface of a mammal, whether or not the skin is intact or open. In some embodiments, the dermal patches of the present invention can exhibit wound healing properties.

In another embodiment, the composition of the present invention is in a spray dosage form. In another embodiment, the spray of the present invention is in an oily vehicle. In another embodiment, the spray of the present invention is in an aqueous vehicle. In another embodiment, the spray of the present invention produces coarse droplets. In another embodiment, the spray of the present invention produces fine droplets. In another embodiment, the DNA polymerase inhibitor of the present invention is dissolved in the spray. In another embodiment, the DNA polymerase inhibitor of the present invention is dispersed in a spray.

In another embodiment, the composition of the present invention is in a gel dosage form. In another embodiment, the gel composition is in a liquid form. In another embodiment, the gel composition is in a soft gel form. In another embodiment, the gel composition is in a semi-solid form. In another embodiment, the gel composition is in a solid form. In another embodiment, the DNA polymerase inhibitor of the present invention is dissolved in the gel. In another embodiment, the DNA polymerase inhibitor of the present invention is dispersed in a gel.

In some embodiments, a gel composition is transparent. In another embodiment, the gel of the present invention provides controlled release of the DNA polymerase inhibitor of the present invention. In another embodiment, a gel composition of the present invention moisturizes the skin and exhibit water wash-off resistance.

In another embodiment, a gel composition is made by mixing one or more compounds to be gelled with a gelling agent. In another embodiment, a gel composition is then combined with or loaded with a relatively low viscosity solvent. In another embodiment, the gel composition is combined with a solvent to produce a resulting gel composition having an increased viscosity.

In another embodiment, Cidofovir is compounded in a gel, and Beeler base (cetyl alcohol 15 g, white wax 1 g, propyleneglycol 10 g, sodium lauryl sulfate 2 g, and water 72 g).

In another embodiment, the composition of the present invention is in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

In another embodiment, the composition of the present invention includes incorporation of DNA polymerase inhibitor of the present invention into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) In some embodiments, such compositions will influence the physical state, solubility, stability, rate of in vivo release, and rate of in vivo clearance. In another embodiment, the composition of the present invention includes incorporation of DNA polymerase inhibitor of the present invention into or onto nanocapsules or nanospheres. In another embodiment, the method of the present invention comprises the use of nanotechnology methods for the preparation of the formulations of the present invention. In another embodiment, the composition of the present invention includes incorporation of DNA polymerase inhibitor of the present invention into or onto particulate preparations which promote transdermal drug delivery. In another embodiment, the composition of the present invention includes incorporation of DNA polymerase inhibitor of the present invention into or onto particulate preparations which promote intralesional drug delivery.

In some embodiments, the pharmaceutical composition of the present invention includes a preservative, antioxidant, buffering agent, acidifying agent, alkalizing agent, antibacterial agent, antifungal agent, solubility enhancing agent, complexation enhancing agent, solvent, electrolyte, salt, water, stabilizer, tonicity modifier, antifoaming agent, oil, emulsifying agent, bulking agent, cryoprotectant or a combination thereof.

"Alkalizing agent" refers, in another embodiment, to a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens and others known to those of ordinary skill in the art. Particularly useful preservatives include EDTA, pentetate, and combinations thereof.

As used herein, the term "antioxidant" is intended to mean an agent that inhibits oxidation and thus is used to prevent the deterioration of preparations by the oxidative process. Such compounds include, by way of example and without limitation, acetone sodium bisulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, citric acid, maleic acid, monobasic sodium phosphate, dibasic sodium phosphate, lactic acid, tartaric acid, potassium metaphosphate, potassium phosphate, monobasic sodium acetate, sodium bicarbonate, sodium tartrate and sodium citrate anhydrous and dihydrate and others known to those of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. In another embodiment, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the lyophilized product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

"Emulsifier" or "emulsifying agent" refer, in another embodiment, to a compound added to one or more of the phase components of an emulsion for the purpose of stabilizing the droplets of the internal phase within the external phase. Such compounds include, by way of example and without limitation, lecithin, polyoxyethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, carboxymethyl cellulose sodium, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

In another embodiment, the formulation of the invention can also include water, organic solvent(s) and combinations thereof. In another embodiment, the formulation includes alcohol, and saline.

In another embodiment, the chemical stability of the liquid formulation varies with pH, thus proper selection of pH is necessary for a stable preparation. In another embodiment, the chemical stability of the liquid formulation can also be enhanced by converting the liquid formulation to a solid formulation.

Also comprehended by the invention are compounds modified by the covalent attachment of water-soluble polymers. In another embodiment, water soluble polymers include water soluble natural polymers, water soluble semisynthetic polymers (such as the water soluble derivatives of cellulose) and water soluble synthetic polymers. The natural polymers include polysaccharides such as dextran, inulin, pectins, algin derivatives and agar, and polypeptides such as casein and gelatin. In another embodiment, the semi-synthetic polymers include cellulose derivatives such as methylcellulose, hydroxyethyl cellulose, carboxymethyl cellulose hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. In another embodiment, the synthetic polymers include polyoxyethylene derivatives (polyethylene glycols), polyproline and polyvinyl derivatives (polyvinyl alcohol, polyvinylpyrrolidone and polystyrene sulfonate) and various copolymers of acrylic acid (e.g. carbomer), copolymers of polyethylene glycol and polypropylene glycol. Suitable hydroxy acids include by way of example, and without limitation, citric acid, malic acid, lactic acid, and tartaric acid and others known to those of ordinary skill in the art.

In another embodiment, the DNA polymerase inhibitor of the present invention is an acyclic nucleoside analogue. In another embodiment, the DNA polymerase inhibitor of the present invention is an acyclic nucleotide analogue. In another embodiment, the DNA polymerase inhibitor of the present invention is an acyclic nucleoside phosphonate. In another embodiment, the DNA polymerase inhibitor of the present invention is a viral DNA polymerase inhibitor. In another embodiment, the viral DNA polymerase inhibitor is an acyclic phosphonate cytosine analogue. In another embodiment, the acyclic phosphonate cytosine analogue is cidofovir.

In another embodiment, the DNA polymerase inhibitor of the present invention is a guanine nucleoside analogue. In another embodiment, the guanine nucleoside analogue is acyclovir. In another embodiment, the guanine nucleoside analogue is valacyclovir.

In another embodiment, the DNA polymerase inhibitor of the present invention is a diacetyl ester prodrug of the acyclic guanosine analogue 6-deoxypenciclovir. In another embodiment, the diacetyl ester prodrug of the acyclic guanosine analogue 6-deoxypenciclovir is famciclovir.

In another embodiment, the DNA polymerase inhibitor of the present invention is penciclovir. In another embodiment, penciclovir is penciclovir triphosphate.

In another embodiment, the DNA polymerase inhibitor of the present invention is a fluorinated pyrimidine nucleoside. In another embodiment, the fluorinated pyrimidine nucleoside is trifluridine.

In another embodiment, the DNA polymerase inhibitor of the present invention is an adenine nucleoside analogue. In another embodiment, the adenine nucleoside analogue is vidarabine.

In another embodiment, the DNA polymerase inhibitor of the present invention is an acyclic analogue of 2' deoxyguanosine. In another embodiment, the acyclic analogue of 2' deoxyguanosine is ganciclovir.

In another embodiment, the DNA polymerase inhibitor of the present invention is the L-valyl ester prodrug of ganciclovir. In another embodiment, the L-valyl ester prodrug of ganciclovir is valaganciclovir.

In another embodiment, the DNA polymerase inhibitor of the present invention is an inorganic pyrophosphate analogue. In another embodiment, the inorganic pyrophosphate analogue is foscarnet.

In another embodiment, the DNA polymerase inhibitor of the present invention is derivative of deoxyuridine. In another embodiment, the derivative of deoxyuridine is iodinated derivative of deoxyuridine. In another embodiment, the iodinated derivative of deoxyuridine is idoxuridine.

In another embodiment, the DNA polymerase inhibitor of the present invention is a synthetic cytidine analogue. In another embodiment, the synthetic cytidine analogue is lamivudine.

In another embodiment, the DNA polymerase inhibitor of the present invention is a deoxycytidine analogue. In another embodiment, the deoxycytidine analogue is decitabine. In another embodiment, the deoxycytidine analogue is anti-neoplastic. In another embodiment, the deoxycytidine analogue incorporates into DNA and forms irreversible covalent bonds with DNA-methyltransferases (Mtase) at cytosine sites targeted for methylation. In another embodiment, this leads to DNA synthesis stalling and eventual degradation of DNA-Mtase.

In another embodiment, the deoxycytidine analogue is gemcitabine. In another embodiment, gemcitabine is a nucleoside analog in which the hydrogens on the 2' carbons of deoxycytidine are replaced by fluorides.

In another embodiment, the composition of the present invention provides a mixture of two or more DNA polymerase inhibitors of the invention.

In another embodiment, the present invention further provides additional active compounds combined with the DNA polymerase inhibitors of the present invention. In another embodiment, the additional active compound is an antibiotic. In another embodiment, the antibiotic compound is an antibacterial compound. In another embodiment, the antibiotic compound is an antiviral compound. In another embodiment, the antibiotic compound is an antifungal compound. In another embodiment, the antibiotic compound is an antiprotozoal compound. In another embodiment, the additional active compound is an antiseptic compound. In another embodiment, the additional active compound is an analgesic compound. In another embodiment, the additional active compound is an anesthetic compound. In another embodiment, the additional active compound is a sedative. In another embodiment, the additional active compound is an anti-inflammatory compound. In another embodiment, the additional active compound is a vitamin.

In another embodiment, the formulation of the present invention would have increased stability and efficacy. In another embodiment, the formulation of the present invention would have decreased side effect profile of the drug which is being used. In another embodiment, the formulation of the present invention would have increased cosmetic acceptability.

In another embodiment, the present invention provides a method of inducing alopecia in a subject, comprising topically administering a composition comprising a DNA polymerase inhibitor. In another embodiment, the present invention provides a method of inducing hair loss in a subject, comprising topically administering a composition comprising a DNA polymerase inhibitor. In another embodiment, a subject of the present invention is a human subject. In another embodiment, a subject of the present invention is a mammal or a farm animal.

In another embodiment, the present invention provides a method removing hair in a subject. In another embodiment, the present invention provides a method of performing epilation. In another embodiment, the present invention provides a method of inducing alopecia. In another embodiment, the term "alopecia" refers to hair loss. In another embodiment, the term refers to baldness. In another embodiment, the term comprises baldness. In another embodiment, alopecia is induced by topically administering the composition of the present invention onto the desired treated body surface or skin area. In another embodiment, alopecia is induced in the head by topically administering the composition of the present invention onto the desired head surfaces to be treated. In another embodiment, alopecia is induced in the arms by topically administering the composition of the present invention onto the desired arms surfaces to be treated. In another embodiment, alopecia is induced in the shoulders by topically administering the composition of the present invention onto the desired shoulders surfaces to be treated. In another embodiment, alopecia is induced in the armpits by topically administering the composition of the present invention onto the desired armpits surfaces to be treated. In another embodiment, alopecia is induced in the hands by topically administering the composition of the present invention onto the desired hands surfaces to be treated. In another embodiment, alopecia is induced in the legs by topically administering the composition of the present invention onto the desired legs surfaces to be treated. In another embodiment, alopecia is induced in the face by topically administering the composition of the present invention onto the desired face surfaces to be treated. In another embodiment, alopecia is induced in the back by topically administering the composition of the present invention onto the desired back surfaces to be treated. In another embodiment, alopecia is induced in the belly by topically administering the composition of the present invention onto the desired belly surfaces to be treated. In another embodiment, alopecia is induced in the chest by topically administering the composition of the present invention onto the desired chest surfaces to be treated. In another embodiment, alopecia is induced in the neck by topically administering the composition of the present invention onto the desired neck surfaces to be treated. In another embodiment, alopecia is induced in the feet by topically administering the composition of the present invention onto the desired feet surfaces to be treated. In another embodiment, alopecia is induced in the genitalia by topically administering the composition of the present invention onto the desired genitalia surfaces to be treated. In another embodiment, alopecia is induced in the buttocks by topically administering the composition of the present invention onto the desired buttocks surfaces to be treated. In another embodiment, alopecia is induced in the perineum by topically administering the composition of the present invention onto the desired perineum surfaces to be treated. In another embodiment, alopecia is induced in the perianal region by topically administering the composition of the present invention onto the desired perianal surfaces to be treated. In another embodiment, alopecia is induced in the groin by topically administering the composition of the present invention onto the desired groin surfaces to be treated. In another embodiment, alopecia is induced in the trunk by topically administering the composition of the present invention onto the desired trunk surfaces to be treated. In another embodiment, alopecia is induced in the ears by topically administering the composition of the present invention onto the desired ears surfaces to be treated. In another embodiment, alopecia is induced in the scalp by topically administering the composition of the present invention onto the desired scalp surfaces to be treated. In another embodiment, alopecia is induced in the fingers by topically administering the composition of the present invention onto the desired fingers surfaces to be treated. In another embodiment, alopecia is induced in the toes by topically administering the composition of the present invention onto the desired toes surfaces to be treated. In another embodiment, alopecia is induced in the eyelids by topically administering the composition of the present invention onto the desired eyelids surfaces to be treated. In another embodiment, alopecia is induced in the eyebrows by topically administering the composition of the present invention onto the desired eyebrows surfaces to be treated. In another embodiment, alopecia is induced in the lips by topically administering the composition of the present invention onto the desired lips surfaces to be treated. In another embodiment, alopecia is induced in any body surface by topically administering the composition of the present invention onto the desired body surface to be treated. In another embodiment, alopecia is induced in multiple body surfaces by topically administering the composition of the present invention onto the desired multiple body surfaces to be treated.

In another embodiment, alopecia occurs within 6 months after the initial use of the composition of the present invention. In another embodiment, alopecia occurs within 4 months after the initial use of the composition of the present invention. In another embodiment, alopecia occurs within 3 months after the initial use of the composition of the present invention. In another embodiment, alopecia occurs within 2 months after the initial use of the composition of the present invention. In another embodiment, alopecia occurs within a month after the initial use of the composition of the present invention. In another embodiment, alopecia occurs within 3 weeks after the initial use of the composition of the present invention. In another embodiment, alopecia occurs within 2 weeks after the initial use of the composition of the present invention. Each possibility represents a separate embodiment of the present invention.

"Topically administering" refers, in another embodiment, to the direct laying on or spreading of, a composition on epidermal tissue at the affected site of the epidermal tissue. In another embodiment, administering the composition of the present invention comprises contacting the desired body surface area with the composition. In another embodiment, administering the composition of the present invention comprises rubbing the composition against a desired body surface area. In another embodiment, administering the composition of the present invention comprises massaging the desired body surface area with the composition. In another embodiment, the composition is applied to the desired area by hand. In another embodiment, the composition is applied to the desired area by an applicator. In another embodiment, the composition is applied to the desired using a gauze.

In another embodiment, the present invention provides a method of inhibiting hair growth in a subject, comprising topically administering a composition comprising a DNA polymerase inhibitor, thereby inhibiting hair growth.

In another embodiment, "inhibiting hair growth" refers to inhibiting the rate of hair growth. In another embodiment, "inhibiting hair growth" refers to delaying hair germination. In another embodiment, the methods of the present invention provide at least a 10% time delay in hair germination. In another embodiment, the methods of the present invention provide at least a 20% time delay in hair germination. In another embodiment, the methods of the present invention provide at least a 30% time delay in hair germination. In another embodiment, the methods of the present invention provide at least a 40% time delay in hair germination. In another embodiment, the methods of the present invention provide at least a 50% time delay in hair germination. In another embodiment, the methods of the present invention provide at least a 60% time delay in hair germination. In another embodiment, the methods of the present invention provide at least a 70% time delay in hair germination. In another embodiment, the methods of the present invention provide at least an 80% time delay in hair germination. In another embodiment, the methods of the present invention provide at least a 90% time delay in hair germination.

In another embodiment, "inhibiting hair growth" refers to lengthening hair cycle. In another embodiment, the methods of the present invention provide at least a 10% time prolongation in hair cycle. In another embodiment, the methods of the present invention provide at least a 20% time prolongation in hair cycle. In another embodiment, the methods of the present invention provide at least a 30% time prolongation in hair cycle. In another embodiment, the methods of the present invention provide at least a 40% time prolongation in hair cycle. In another embodiment, the methods of the present invention provide at least a 50% time prolongation in hair cycle. In another embodiment, the methods of the present invention provide at least a 60% time prolongation in hair cycle. In another embodiment, the methods of the present invention provide at least a 70% time prolongation in hair cycle. In another embodiment, the methods of the present invention provide at least an 80% time prolongation in hair cycle. In another embodiment, the methods of the present invention provide at least a 90% time prolongation in hair cycle. In another embodiment, the methods of the present invention provide at least a 150% time prolongation in hair cycle. In another embodiment, the methods of the present invention provide at least a 300% time prolongation in hair cycle. In another embodiment, the methods of the present invention provide at least a 500% time prolongation in hair cycle. In another embodiment, the methods of the present invention provide at least a 1000% time prolongation in hair cycle.

In another embodiment, "inhibiting hair growth" refers to lengthening telogen. In another embodiment, the methods of the present invention provide at least a 10% time extension in telogen phase. In another embodiment, the methods of the present invention provide at least a 20% time extension in telogen phase. In another embodiment, the methods of the present invention provide at least a 30% time extension in telogen phase. In another embodiment, the methods of the present invention provide at least a 40% time extension in telogen phase. In another embodiment, the methods of the present invention provide at least a 50% time extension in telogen phase. In another embodiment, the methods of the present invention provide at least a 60% time extension in telogen phase. In another embodiment, the methods of the present invention provide at least a 70% time extension in telogen phase. In another embodiment, the methods of the present invention provide at least an 80% time extension in telogen phase. In another embodiment, the methods of the present invention provide at least a 90% time extension in telogen phase. In another embodiment, the methods of the present invention provide at least a 150% time extension in telogen phase. In another embodiment, the methods of the present invention provide at least a 300% time extension in telogen phase. In another embodiment, the methods of the present invention provide at least a 500% time extension in telogen phase. In another embodiment, the methods of the present invention provide at least a 1000% time extension in telogen phase.

In another embodiment, inhibiting hair growth refers to reducing the maximal hair length. In another embodiment, maximal hair length is measured for a given hair before applying the compositions of the present invention. In another embodiment, the methods of the present invention provide between 0.0000001% to 100% reduction in maximal hair length. In another embodiment, the methods of the present invention provide at least 10% reduction in maximal hair length. In another embodiment, the methods of the present invention provide at least 20% reduction in maximal hair length. In another embodiment, the methods of the present invention provide at least 30% reduction in maximal hair length. In another embodiment, the methods of the present invention provide at least 40% reduction in maximal hair length. In another embodiment, the methods of the present invention provide at least 50% reduction in maximal hair length. In another embodiment, the methods of the present invention provide at least 60% reduction in maximal hair length. In another embodiment, the methods of the present invention provide at least 70% reduction in maximal hair length. In another embodiment, the methods of the present invention provide at least 80% reduction in maximal hair length. In another embodiment, the methods of the present invention provide at least 90% reduction in maximal hair length. In another embodiment, the methods of the present invention provide at least 95% reduction in maximal hair length.

In another embodiment, inhibiting hair growth refers to reducing the maximal hair diameter. In another embodiment, maximal hair diameter is measured for a given hair before applying the compositions of the present invention. In another embodiment, the methods of the present invention provide between 0.0000001% to 100% reduction in maximal hair diameter. In another embodiment, the methods of the present invention provide at least 10% reduction in maximal hair diameter. In another embodiment, the methods of the present invention provide at least 20% reduction in maximal hair diameter. In another embodiment, the methods of the present invention provide at least 30% reduction in maximal hair diameter. In another embodiment, the methods of the present invention provide at least 40% reduction in maximal hair diameter. In another embodiment, the methods of the present invention provide at least 50% reduction in maximal hair diameter. In another embodiment, the methods of the present invention provide at least 60% reduction in maximal hair diameter. In another embodiment, the methods of the present invention provide at least 70% reduction in maximal hair diameter. In another embodiment, the methods of the present invention provide at least 80% reduction in maximal hair diameter. In another embodiment, the methods of the present invention provide at least 90% reduction in maximal hair diameter. In another embodiment, the methods of the present invention provide at least 95% reduction in maximal hair diameter.

In another embodiment, administration may be by any number of means as embodied herein. In some embodiments, the composition is in a liquid form. In some embodiments, the composition is in a solid form. In some embodiments, the composition is in a semi-solid form. In some embodiments, administration is via a pump or injection. In another embodiment, delivery is "on-site" such as during surgery, biopsy or other interventionist therapy. In another embodiment, targeted delivery may also be accomplished.

Treatment

In another embodiment, the methods of present invention apply to patients suffering from hormonal imbalance which cause extensive hair growth. In another embodiment, the methods of present invention apply to patients suffering from any disease resulting in extensive hair growth. In another embodiment, the methods of present invention apply to patients that are genetically hairy. In another embodiment, any patient in need of a hair removal procedure is treated by the compositions and methods of the present invention. In another embodiment, the methods of present invention extend to the prophylaxis of hair growth.

In another embodiment, the methods of present invention include applying a lotion comprising the DNA polymerase inhibitor of the invention on a body surface, thereby inducing alopecia in the body surface. In another embodiment, the body surface is skin. In another embodiment, the body surface is a mucus membrane. In another embodiment, a lotion is applied once a day. In another embodiment, a lotion is applied 2-4 times a day. In another embodiment, a lotion is applied 3 times a day.

In another embodiment, the methods of present invention include applying a cream comprising the DNA polymerase inhibitor of the invention on a body surface, thereby inducing alopecia in the body surface. In another embodiment, the body surface is skin. In another embodiment, the body surface is a mucus membrane. In another embodiment, a cream is applied once a day. In another embodiment, a cream is applied 2-4 times a day. In another embodiment, a cream is applied 3 times a day.

In another embodiment, the methods of present invention include applying an ointment comprising the DNA polymerase inhibitor of the invention on a body surface, thereby inducing alopecia in the body surface. In another embodiment, the body surface is skin. In another embodiment, the body surface is a mucus membrane. In another embodiment, an ointment is applied once a day. In another embodiment, an ointment is applied 2-4 times a day. In another embodiment, an ointment is applied 3 times a day.

In another embodiment, the methods of present invention include applying a spray comprising the DNA polymerase inhibitor of the invention on a body surface, thereby inducing alopecia in the body surface. In another embodiment, the body surface is skin. In another embodiment, the body surface is a mucus membrane. In another embodiment, a spray is applied once a day. In another embodiment, a spray is applied 2-4 times a day. In another embodiment, a spray is applied 3 times a day.

In another embodiment, the methods of present invention include applying a gel comprising the DNA polymerase inhibitor of the invention on a body surface, thereby inducing alopecia in the body surface. In another embodiment, the body surface is skin. In another embodiment, the body surface is a mucus membrane. In another embodiment, a gel is applied once a day. In another embodiment, a gel is applied 2-4 times a day. In another embodiment, a gel is applied 3 times a day.

For administration to mammals, and particularly humans, it is expected that a physician will determine the actual dosage and duration of treatment, which will be most suitable for an individual and can vary with the age, weight and response of the particular individual.

In another embodiment, the lotion of the present invention is applied to external skin with bare hands. In another embodiment, the lotion of the present invention is applied to external skin with a plastic wand. In another embodiment, the lotion of the present invention is applied to external skin with a clean cloth. In another embodiment, the lotion of the present invention is applied to external skin with a cotton wool. In another embodiment, the lotion of the present invention is applied to external skin with gauze. In another embodiment, the lotion of the present invention is applied to external skin with a polyester fiber.

In another embodiment, the cream of the present invention is applied to external skin with bare hands. In another embodiment, the cream of the present invention is applied to external skin with a plastic wand. In another embodiment, the cream of the present invention is applied to external skin with a clean cloth. In another embodiment, the cream of the present invention is applied to external skin with a cotton wool. In another embodiment, the cream of the present invention is applied to external skin with gauze. In another embodiment, the cream of the present invention is applied to external skin with a polyester fiber.

In another embodiment, the spray of the present invention is applied to external skin with bare hands. In another embodiment, the spray of the present invention is applied to external skin with a plastic wand. In another embodiment, the spray of the present invention is applied to external skin with a clean cloth. In another embodiment, the spray of the present invention is applied to external skin with a cotton wool. In another embodiment, the spray of the present invention is applied to external skin with gauze. In another embodiment, the spray of the present invention is applied to external skin with a polyester fiber.

In another embodiment, the gel of the present invention is applied to external skin with bare hands. In another embodiment, the gel of the present invention is applied to external skin with a plastic wand. In another embodiment, the gel of the present invention is applied to external skin with a clean cloth. In another embodiment, the gel of the present invention is applied to external skin with a cotton wool. In another embodiment, the gel of the present invention is applied to external skin with gauze. In another embodiment, the gel of the present invention is applied to external skin with a polyester fiber.

In another embodiment, the ointment of the present invention is applied to external skin with bare hands. In another embodiment, the ointment of the present invention is applied to external skin with a plastic wand. In another embodiment, the ointment of the present invention is applied to external skin with a clean cloth. In another embodiment, the ointment of the present invention is applied to external skin with a cotton wool. In another embodiment, the ointment of the present invention is applied to external skin with gauze. In another embodiment, the ointment of the present invention is applied to external skin with a polyester fiber.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

EXAMPLES

Example 1

Cidofovir Induces Alopecia

Formulation

A 3% topical ointment of cidofovir was prepared by mixing 3 g of cidofovir in 97 g of petrolatum.

A 3% topical preparation of cidofovir was applied to the beard area of a male patient. The formulation was applied by the patient once a day to the affected areas of the face for the treatment of verruca vulgaris (warts). The patient developed mild inflammation, at which point he discontinued the application for several days and then resumed it on a once a day basis. After 4-8 weeks the patient had alopecia in the areas of the face where the medication was applied. This was the only hair bearing area that the patient applied the medication to. The warts resolved in approximately 2-3 months. Upon discontinuation of the topical cidofovir, the hair grew back.

The hair cycle time of the face is the shortest on the body. At any one point in time, up to 80% of the hair on the face (i.e. the beard area) is in the active growth phase. Thus, the unexpected results as described herein for the beard area demonstrate the effectiveness of the topical formulations of the present invention.

| EXAMPLE 2: 0.8% CIDOFOVIR CREAM FORMULATION | |
|---|---|
| Cream | Weight |
| Cidofovir | 0.8 g |
| Glycerol | 2.00 g |
| Cetostearyl alcohol | 6.75 g |
| Sodium Lauryl Sulphate | 0.75 g |
| White Soft Paraffin | 12.50 g |
| Liquid Paraffin | 5.00 g |
| Chlorocresol | 0.1 g |
| Purified Water to | 100.00 g |

Cidofovir is dissolved in a mixture of purified water and glycerol and heated to 70° C. The remaining ingredients are heated together at 70° C. The two parts are added together and emulsified. The resulting composition is cooled and filled into containers.

| EXAMPLE 3: 0.5% CIDOFOVIR OINTMENT FORMULATION | |
|---|---|
| Ointment | Weight |
| Cidofovir | 0.5 g |
| Castor Oil, U.S.P | 5.00 g |
| Titanium Dioxide | 0.5 g |
| Plastibase 50W, to | 100.0 g |

0.5 g of cidofovir is dissolved in castor oil by gentle heating not over 90° C. The solution is cooled to room temperature and mixed with 0.2 g of titanium dioxide. 0.5 g of cidofovir is mixed with 0.3 gm of titanium dioxide and dispersed into about 1 gm of Plastibase homogeneously. The resulting concentrate is dispersed geometrically into the remainder of the Plastibase.

The castor oil dispersion is incorporated with about an equal amount of the Plastibase dispersion and mixed thoroughly. The remainder of the Plastibase dispersion is mixed with the castor oil dispersion until a homogeneous mixture is obtained (for about 20 to 30 minutes).

The formulation is prescribed to adult males and females patients once a day for legs hair removal. The treatment is expected to induce alopecia in the treated legs area within about a month of treatment.

EXAMPLE 4: 0.5% ACYCLOVIR CLEAR GEL FORMULATION

| Clear Gel | Weight |
|---|---|
| Acyclovir | 0.5 g |
| Castor Oil, U.S.P | 10.0 g |
| Mineral oil | 79.9 g |
| Paraflint RG | 6.0 g |
| Span 65 | 3.6 g |

Paraflint RG and Span 65 are melted and heated to 90° C. The molten mixture is incorporated in hot (90° C.) mineral oil and mixed well. The temperature of the oil is quickly brought to 50° C. to form a gel.

Acyclovir is dissolved in castor oil by gentle heat, the oil is cooled to room temperature and then is incorporated in the gel homogeneously.

What is claimed is:

1. A method of inducing a transient hair loss in a skin of a subject in need thereof, comprising the step of topically administering to said subject in need thereof a composition comprising an effective amount of a cidofovir, thereby inducing said transient hair loss in said skin of said subject.

2. The method of claim 1, wherein said composition is an ointment.

3. The method of claim 1, wherein said composition is a lotion.

4. The method of claim 1, wherein said composition is a cream.

5. The method of claim 1, wherein said composition is a spray.

6. The method of claim 1, wherein said composition is a gel.

7. The method of claim 1, wherein said subject is human subject.

8. The method of claim 1, wherein the concentration of said cidofovir in said composition ranges from about 0.1% to about 5% w/w.

* * * * *